US009526869B2

(12) United States Patent
Beran

(10) Patent No.: US 9,526,869 B2
(45) Date of Patent: Dec. 27, 2016

(54) CATHETER SECUREMENT DEVICE

(71) Applicant: Anthony V Beran, Yorba Linda, CA (US)

(72) Inventor: Anthony V Beran, Yorba Linda, CA (US)

( * ) Notice: Subject to any disclaimer, the term of this patent is extended or adjusted under 35 U.S.C. 154(b) by 47 days.

(21) Appl. No.: 13/986,351

(22) Filed: Apr. 23, 2013

(65) Prior Publication Data

US 2014/0316339 A1 Oct. 23, 2014

(51) Int. Cl.
*A61M 5/32* (2006.01)
*A61M 25/02* (2006.01)

(52) U.S. Cl.
CPC ........ *A61M 25/02* (2013.01); *A61M 2025/024* (2013.01); *A61M 2025/026* (2013.01); *A61M 2025/0266* (2013.01)

(58) Field of Classification Search
CPC ................ A61M 2025/0206; A61M 2025/024
USPC .......................................................... 604/180
See application file for complete search history.

(56) References Cited

U.S. PATENT DOCUMENTS 4,008,512 A * 2/1977 Prodel ................... F16L 3/2334
24/16 PB
8,025,643 B2 * 9/2011 Bierman ....................... 604/174
2014/0142538 A1 * 5/2014 Hyman ............... A61F 13/0216
604/500

* cited by examiner

*Primary Examiner* — Kevin C Sirmons
*Assistant Examiner* — Deanna K Hall
(74) *Attorney, Agent, or Firm* — Gordon E. Gray, III; Gray Law Firm

(57) ABSTRACT

The present invention pertains to a device for securing a medical implement to the body of a patient such as a catheter. The device preferably comprises a base pad with at least a portion of the bottom surface having adhesive thereon for attaching the device to the body of the patient. The device also has a securement member attached to the base pad. The securement member preferably has a rigid member base with a flexible gear rack extending from one side and an adjustable locking device extending from the other side. The locking device is adjustably lockable to the gear rack by a lock case with a ratchet and at least one open side. A center pad is mounted on the rigid member base and a lock pad is mounted adjacent to the locking device. The base pad can also further comprise a transparent window.

6 Claims, 5 Drawing Sheets

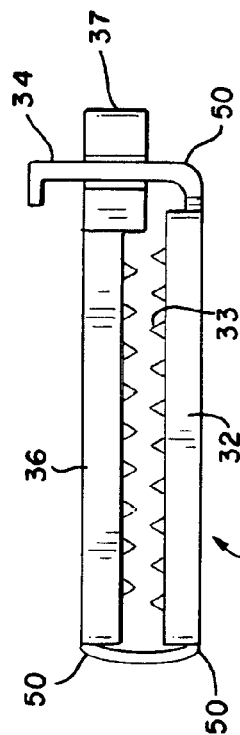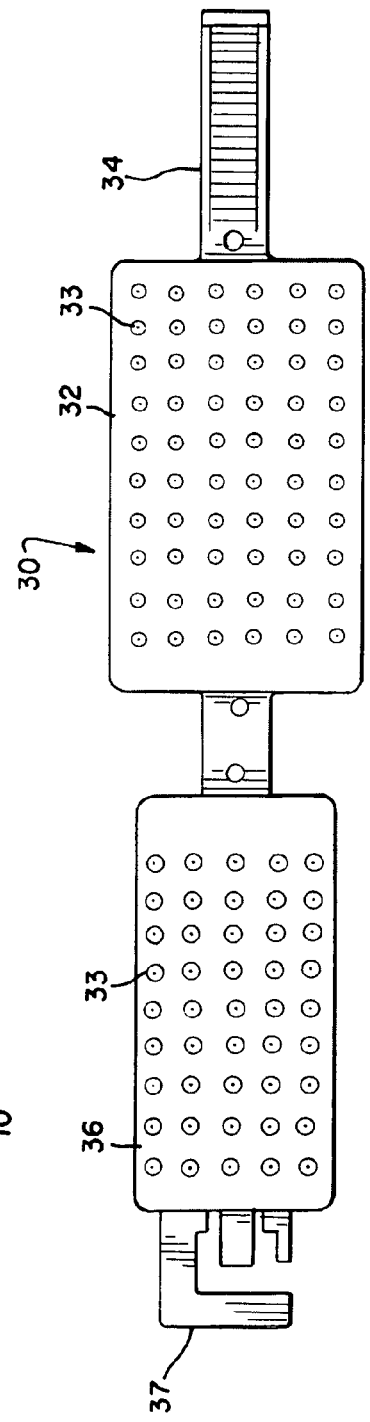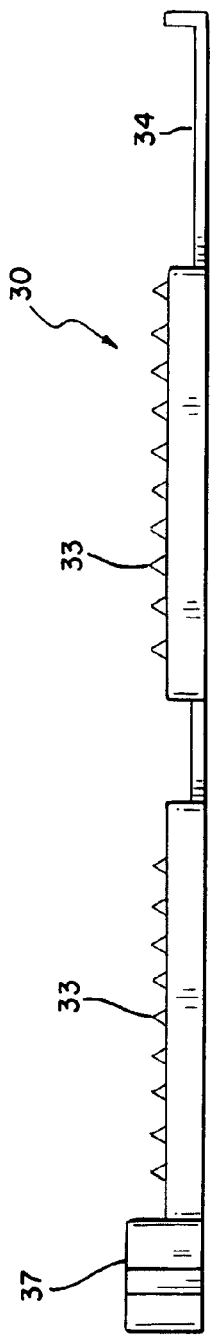
FIG. 7
FIG. 8
FIG. 9

CATHETER SECUREMENT DEVICE

TECHNICAL FIELD

The present invention pertains to a device for securing a medical implement to the body of a patient such as a catheter.

BACKGROUND ART

Medical implements such as catheters, tubes and lines often must be used on patients and left in place. Accordingly, these items can be attached to a patient by various devices such as those disclosed in U.S. Pat. Nos. 7,922,697 and 4,392,857.

However, these devices can be either overly complex, bulky or not compatible with various medical implements. Thus, a simpler and more versatile securement device is desired.

SUMMARY OF THE INVENTION

The present invention pertains to a device for securing a medical implement to the body of a patient such as a catheter. The device preferably comprises a base pad with at least a portion of the bottom surface having adhesive thereon for attaching the device to the body of the patient. The device also has a securement member attached to the base pad. The securement member preferably has a rigid member base with a flexible gear rack extending from one side and an adjustable locking device extending from the other side. The locking device is adjustably lockable to the gear rack by a lock case with a ratchet and at least one open side. A center pad is mounted on the rigid member base and a lock pad is mounted adjacent to the locking device. The base pad can also further comprise a transparent window. The securement device geometry (length and width) is selected to fit catheters of different configuration and size by choosing the number and location of living hinges.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 7 is a side view of an alternative embodiment of the invention without pads in a closed position;

FIG. 8 is a top view of an alternative embodiment of the invention without pads in an open position; and, FIG. 9 is a side view of an alternative embodiment of the invention without pads in an open position.

DETAILED DESCRIPTION OF THE PREFERRED EMBODIMENTS

Figure 1:
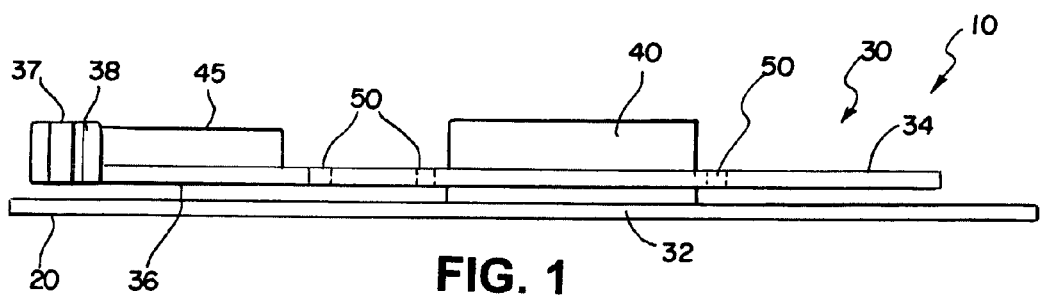
FIG. 1 is a side view of a preferred embodiment of the invention in an open position.

Various embodiments are now described with reference to the drawings, wherein like reference numerals are used to refer to like elements throughout. In the following description, for purposes of explanation, numerous specific details are set forth in order to provide a thorough understanding of one or more embodiments. It may be evident, however, that such embodiment(s) may be practiced without these specific details.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s). The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved catheter securement device.

Referring now to FIG. 1, a side view of a preferred embodiment of the invention 10 is shown in an open position. The preferred embodiment shown in FIG. 1 has a base pad 20 with a top and bottom surface, where at least a portion of the bottom surface of the pad 20 has an adhesive. The adhesive is preferably suitable for attaching the device to the body of a patient and can be any hypoallergenic adhesive suitable for skin application.

Figure 3:
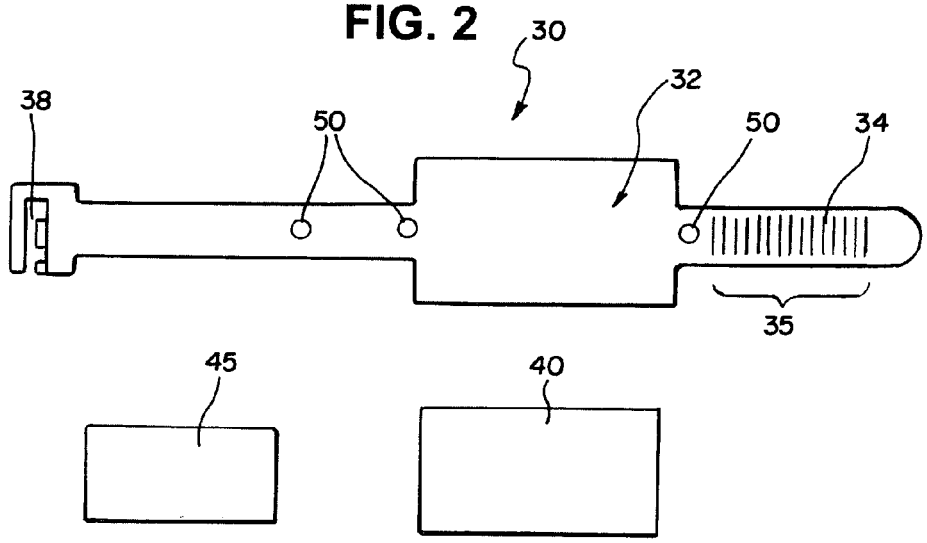
FIG. 3 is a top partially exploded view of a preferred embodiment of the securement member.

A securement member 30 is preferably attached to the top surface of the base pad 20. The securement member 30 shown in FIG. 1 has a member base 32 with a gear rack 34 extending from a first side and a locking device 36 extending from a second side. The gear rack 34 shown in FIG. 1 is connected to the member base 32 by a living hinge 50. The locking device 36 shown in FIG. 1 is connected to the member base by a set of living hinges 50. The gear rack 34 preferably has notches 35 as shown in FIG. 3. The notches 35 are preferably used to interact with the locking device 36. The locking device 36 shown has a lock case 37 with an open side and a ratchet 38, where the ratchet 38 engages with the notches 35. The locking device 36 can be adjusted by disengaging the ratchet 38 from the notches 35, e.g. using the open side of the lock case 37.

A center pad 40 is preferably mounted on the member base 32. The center pad 40 is preferably a foam pad with a plastisol sleeve or plastisol film coating, or a non-skid pliable plastic material. A lock pad 45 is preferably mounted on the locking device 36 next to the lock 37. The lock pad 45 is preferably a foam pad with a plastisol sleeve or plastisol film coating, or a non-skid pliable plastic material. The securement member 30 is preferably a single integrated unit created by injection molding of plastic such as nylon. The member base 32 is preferably rigid and the locking device 36 and gear rack 34 are preferably flexible.

Figure 2:
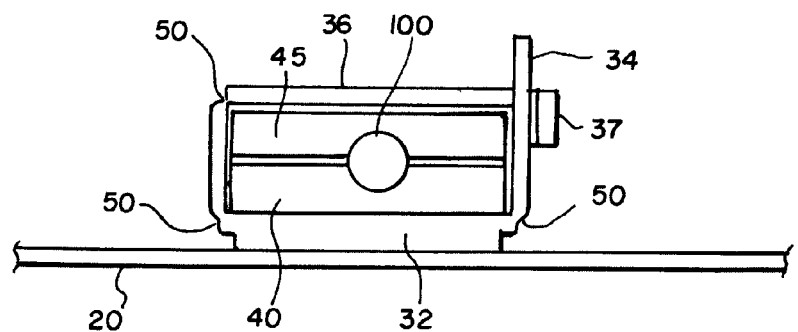
FIG. 2 is a side view of a preferred embodiment of the invention in a closed position.

Referring now to FIG. 2, a side view of the preferred embodiment shown in FIG. 1 is shown in the closed position. As shown, the gear rack 34 is insert through the lock case 37 on the locking device 36. The gear rack 34 is preferably held in the lock case 37 by the engagement of the ratchet 38 on the notches 35 of the gear rack 34. The securement member 30 can be adjusted for a looser or tighter fit around a medical implement, e.g. a catheter 100, using the gear rack 34 and lock case 37 with ratchet 38. Preferably, the pads 40 and 45 are deformable around the implement 100 for a tighter hold on the implement 100. The living hinges 50 preferably bend to allow the securement member 30 to move between the open position in FIG. 1 and the closed position in FIG. 2, and depending on the location and number of living hinges 50, the hinges 50 allow the securement member 30 to form a desired geometry to secure objects of different geometry and size. The living hinges 50 allow the invention to close into a more compact form, namely the closed position, while keeping the device simple in operation.

Figure 4:
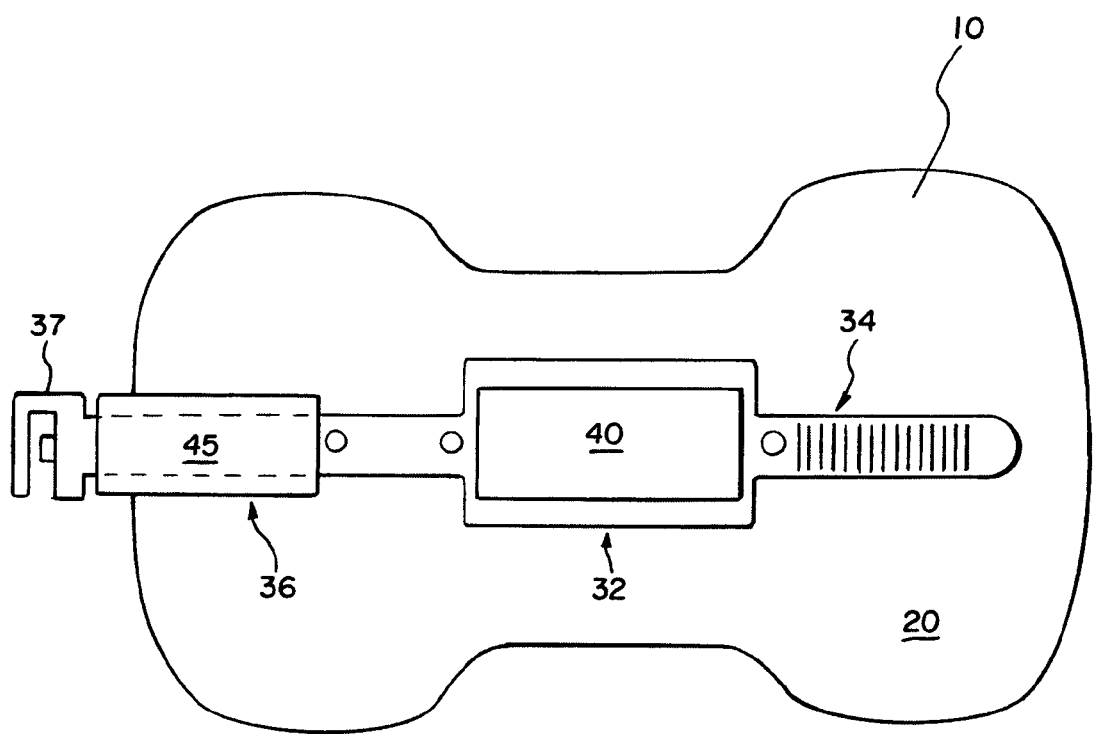
FIG. 4 is a top view of a preferred embodiment of the invention in an open position.
Figure 6:
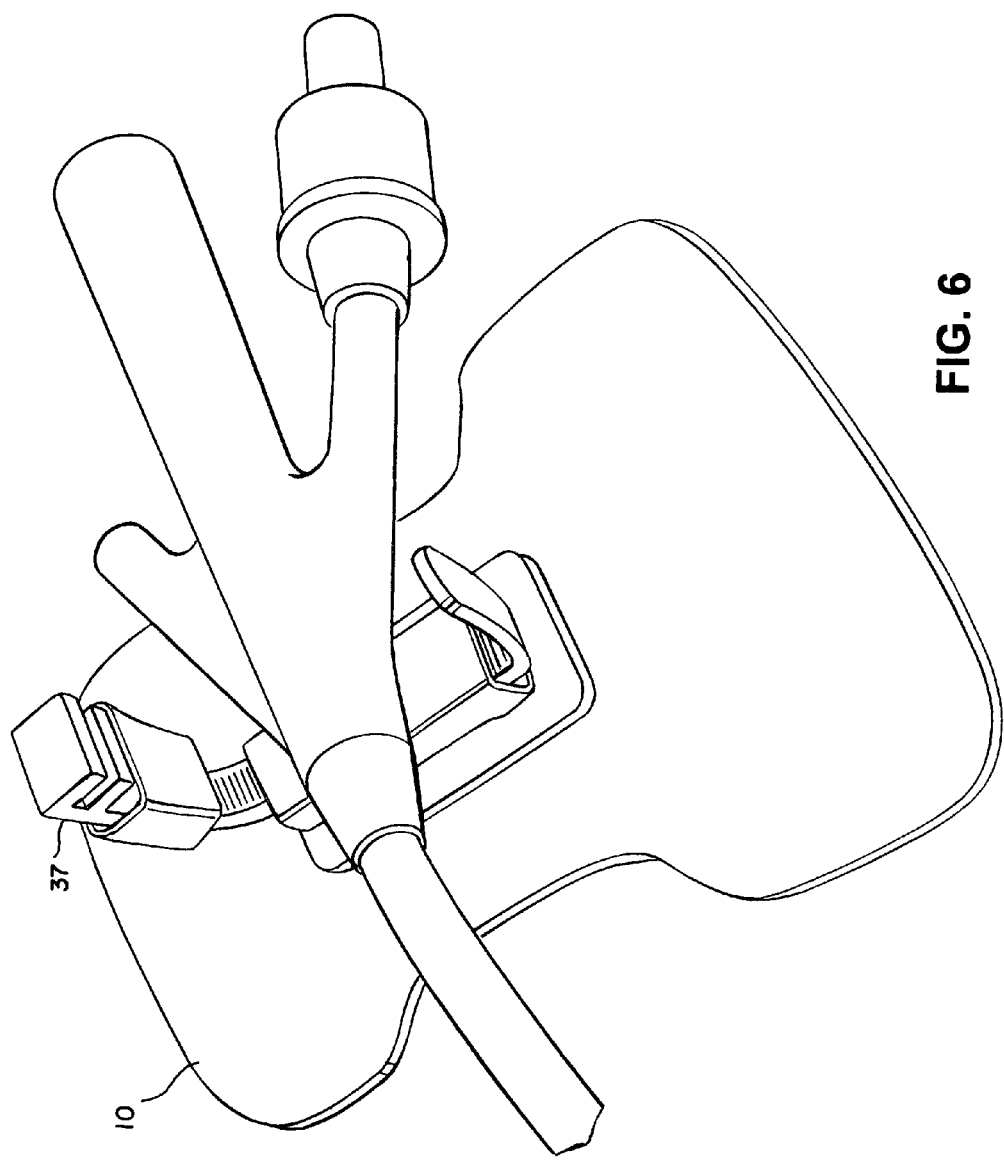
FIG. 6 is a top perspective view of a preferred embodiment of the invention in an open position with a catheter in place.

Referring now to FIG. 4, a top view of a preferred embodiment of the invention 10 is shown in an open position. The preferred embodiment shown in FIG. 4 is preferably for use to secure a central venous catheter and/or other catheters or tubes. FIG. 6 shows a preferred embodiment in an open position with a catheter in place.

Figure 5:
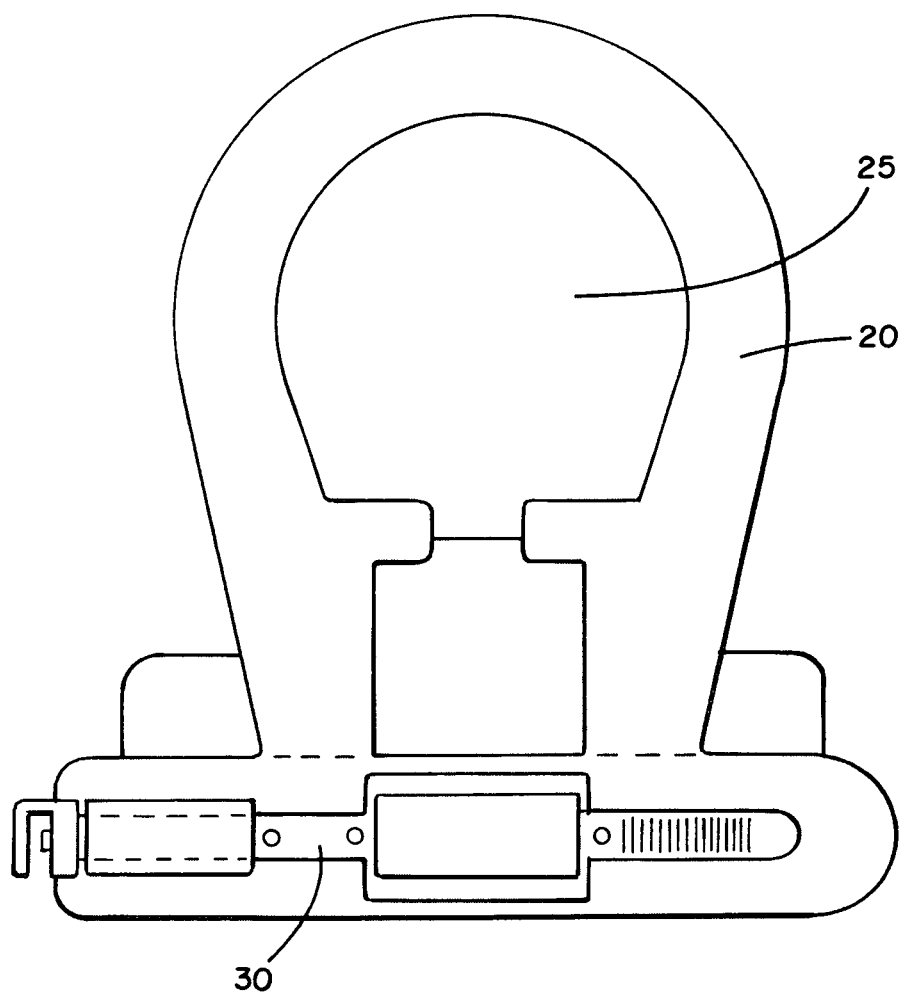
FIG. 5 is a top view of an alternative embodiment of the invention where the base pad further comprises a transparent window.

Referring now to FIG. 5, a top view of another preferred embodiment of the invention 10 is shown in an open position. In FIG. 5, the alternative embodiment is preferably used for securement of peripheral intravenous ("IV") catheters and/or line. The base pad 20 still preferably uses an adhesive on its bottom side for attachment to a patient. However, the base pad 20 further comprises a transparent window 25 with hypoallergenic adhesive, where the window 25 is usually made of clear urethane co-polyester film. The securement member 30 is then preferably mounted at the perimeter of the pad 20.

Referring now to FIG. 7, another alternative embodiment of the securement member 30 is shown in a closed position. This alternative embodiment preferably does not use pads as described above. Instead, the member base 32 and locking device 36 have teeth 33 protruding from interior surfaces, namely the base securement and lock securement surfaces. The alternative embodiment is shown in open position in FIGS. 8 and 9. The teeth 33 or other protrusions such as bumps preferably are used to grip items in the device such as medical implements, pads or bandages. Again, the alternative embodiment shown in FIGS. 7-9 preferably has living hinges 50 that allow the securement member 30 to be more compactly closed into different sizes and geometries.

Thus, an improved catheter securement device is described above that is less bulky, simpler, more flexible and more compact. In each of the above embodiments, the different positions and structures of the present invention are described separately in each of the embodiments. However, it is the full intention of the inventor of the present invention that the separate aspects of each embodiment described herein may be combined with the other embodiments described herein. Those skilled in the art will appreciate that adaptations and modifications of the just-described preferred embodiment can be configured without departing from the scope and spirit of the invention. Therefore, it is to be understood that, within the scope of the appended claims, the invention may be practiced other than as specifically described herein.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A securement device for securing a medical implement to the body of a patient, the securement device comprising:
   a base pad having a top surface and a bottom surface, at least a portion of the bottom surface having adhesive thereon for attaching the securement device to the body of the patient;
   a securement member attached to the base pad, the member having a member base with a first and an opposing second side and a base securement surface, a gear rack extending from the first side and a locking device extending from the opposing second side and having a lock securement surface, where the locking device is lockable to the gear rack; where the gear rack has a plurality of notches such that the securement member is adjustable;
   where the gear rack is connected to the first side of the member base by at least one living hinge and where the locking device is connected to the second side of the member base by at least one multi-directional articulation member comprising at least two living hinges and a transverse member, whereby the number and the location of living hinges will provide a geometrical configuration suitable for device securement in application mode; and
   the base securement surface comprising a base plate wider than the gear rack and a non-skid adhesive surface and the lock securement surface comprising a lock plate wider than the gear rack and a non-skid adhesive surface.

2. A securement device for securing a medical implement to the body of a patient, the securement device comprising:
   a base pad having a top surface and a bottom surface, at least a portion of the bottom surface having adhesive thereon for attaching the securement device to the body of the patient;
   a securement member attached to the base pad, the member having a member base with a first and second side and a base securement surface, a gear rack extending from the first side and a locking device extending from the second side and having a lock securement surface, where the locking device is lockable to the gear rack; and,
   where the gear rack is connected to the first side of the member base by at least one living hinge and where the locking device is connected to the second side of the member base by another at least two living hinges connected by at least one traverse member, whereby the number and the location of living hinges will provide a geometrical configuration suitable for device securement in application mode.

3. A securement device having a base and a cover, where the cover articulates with the base by a joint action of a first and second living hinge and a solid transverse member providing for lateral, longitudinal and transverse movement of the cover in relationship to the base when the device is in a lock position to secure a medical implement between the base and the cover;
   where the first living hinge is positioned between the base and the transverse member;
   where the first living hinge provides for movement of the transverse member laterally causing the cover to move laterally in both directions in relationship to the base;
   where the second living hinge is positioned between the transverse member and the cover;
   where the second living hinge provides the transverse movement of the cover in both directions in relationship to the base;
   where a combined structure of the first living hinge, transverse member and second living hinge provide for transverse, lateral and longitudinal movement of the cover in relationship to the base;
   where a locking device extends from the cover opposite to the second living hinge; and,
   where the locking device is lockable to a gear rack.

4. The securement device of claim 3 further comprising a third living hinge and gear rack;
   where the third living hinge is positioned between the gear rack and the base;
   where the third living hinge provides for lateral movement of the gear rack in relationship to the base;
   where the cover locks to the base by joint action of the third living hinge, gear rack and locking device's ratchet, permitting the cover to acquire multiple lateral and transverse positions in relationship to the base to secure a medical implement between the base and the cover.

5. The securement device of claim 4, further comprising of a locking case extending from the locking device with a side opening perpendicular to the surface of the locking device;
   where the side opening is configured such that the gear rack may be inserted sideways into the lock case when the ratchet of the lock case is aligned with the gear rack;

where the cover moves longitudinally to and from the base, permitting the gear rack to slide and to engage longitudinally into the locking case of the locking device cover.

6. The securement device of claim 5, where the locking device cover acquires the lock position along multiple points on the gear rack by applying transverse force on the cover towards the base.

* * * * *